(12) United States Patent
Degelaen et al.

(10) Patent No.: US 8,106,155 B2
(45) Date of Patent: *Jan. 31, 2012

(54) TEST KIT FOR DETERMINING PROCESS FOR DETERMINING ANTIBIOTICS CONTAINING A BETA-LACTAM RING IN A BIOLOGICAL FLUID

(75) Inventors: Jacques Degelaen, Genappes (BE); Benoît Granier, Esneux (BE); Jean-Marie Frere, Nantrin (BE); Bernard Joris, Spa (BE)

(73) Assignee: Neogen Corporation, Lansing, MI (US)

( * ) Notice: Subject to any disclaimer, the term of this patent is extended or adjusted under 35 U.S.C. 154(b) by 2517 days.

This patent is subject to a terminal disclaimer.

(21) Appl. No.: 10/170,343

(22) Filed: Jun. 14, 2002

(65) Prior Publication Data

US 2002/0192715 A1  Dec. 19, 2002

Related U.S. Application Data

(62) Division of application No. 09/276,923, filed on Mar. 26, 1999, now Pat. No. 6,524,804.

(30) Foreign Application Priority Data

Jun. 25, 1998 (BE) .................. 9800485

(51) Int. Cl.
*G01N 33/567* (2006.01)
(52) U.S. Cl. ......... 530/350; 435/7.2; 435/7.1; 435/7.32; 435/174; 436/518; 436/524; 436/43
(58) Field of Classification Search .............. None
See application file for complete search history.

(56) References Cited

U.S. PATENT DOCUMENTS

| | | | |
|---|---|---|---|
| 4,239,852 A | 12/1980 | Charm | |
| 4,762,782 A | 8/1988 | Goldberg | |
| 5,434,053 A | 7/1995 | Piasio | |
| 6,319,466 B1 | 11/2001 | Markovsky et al. | |
| 6,475,805 B1 | 11/2002 | Charm et al. | |

OTHER PUBLICATIONS

Joris et al., FEMS Microbiology Letters, vol. 70, 1990, pp. 107-114.
Zhu et al., Journal of Bacteriology, vol. 172, No. 2, Feb. 1990, pp. 1137-1141.

*Primary Examiner* — Robert A Zeman
(74) *Attorney, Agent, or Firm* — Ian C. McLeod

(57) ABSTRACT

A test kit for detecting an antibiotic or antibiotics containing a β-lactam ring in a biological fluid is provided. The test kit includes at least one recognition agent, which is a receptor which specifically binds to antibiotics containing a β-lactam ring and is obtained from *Bacillus licheniformis*. The test kit further contains at least one reference antibiotic immobilized on a solid support.

20 Claims, 1 Drawing Sheet

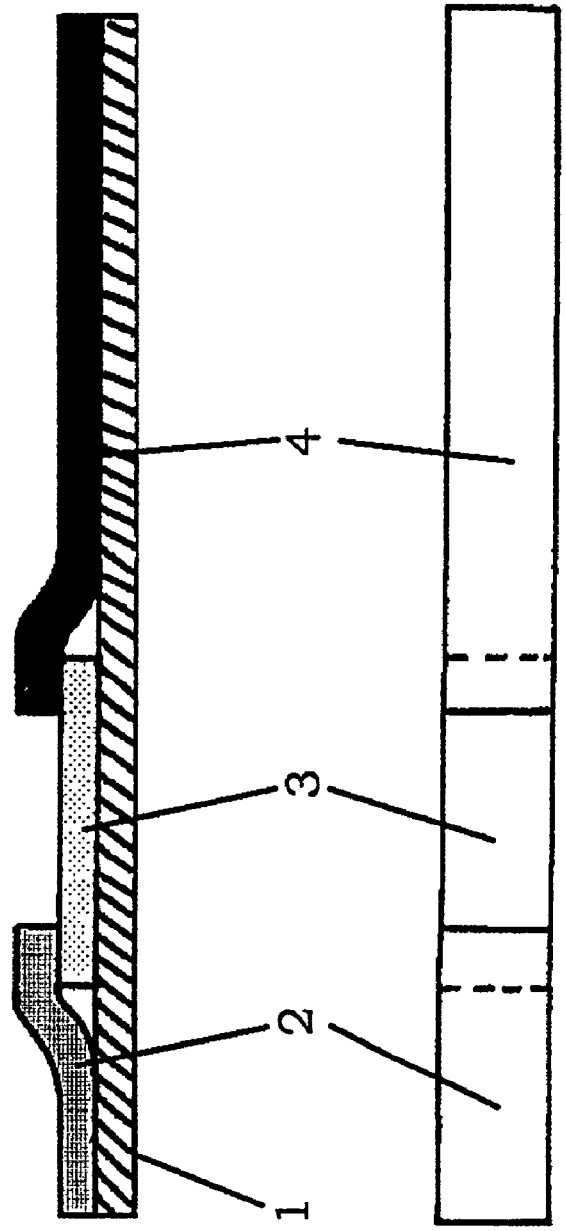

TEST KIT FOR DETERMINING PROCESS FOR DETERMINING ANTIBIOTICS CONTAINING A BETA-LACTAM RING IN A BIOLOGICAL FLUID

This application is a divisional of Ser. No. 09/276,923 filed Mar. 26, 1999, now U.S. Pat. No. 6,524,804.

The present invention relates to novel, rapid and sensitive processes for determining antibiotics containing a β-lactam ring in a biological fluid, using a receptor which is sensitive to the antibiotics containing a β-lactam ring of *Bacillus licheniformis*. The invention also relates to kits for carrying out these processes.

At the present time, antibiotics are very widely used, not only as therapeutic agents in the treatment of infectious diseases caused by bacteria, but also as agents for storing foods and as additives in animal feed to stimulate growth. The need is thus increasingly being felt to be able to detect the presence of antibiotics, even in very low concentrations, in complex biological fluids, such as milk, urine, blood, serum, saliva, meat extracts, fermentation liquids or in buffered aqueous media.

The case of milk production is an example of this, since it is well known to use antibiotics to treat certain infectious diseases of dairy cattle.

However, for obvious medical reasons, milk intended for human consumption must, in principle, be free of any trace of antibiotics. Moreover, penicillin concentrations of 0.005 I.U./ml or less can have harmful effects during the manufacture of milk-based products such as cheese, yoghurt, etc.

Several situations may be envisaged. In a first case, for example to detect the presence of antibiotics at the farm before transferring into a wagon, priority will be given to an extremely rapid (less than 5 minutes) and simple test. It may also be possible to envisage using such a rapid test when, for example, the antibiotic which has been used for the treatment is known and when, moreover, this test allows the detection of the antibiotic in question at the legal standard. In the second case, when the emphasis is not on speed, the importance is to detect most, if not all, of the antibiotics at the legal standards.

The reason for this is that the laws in certain countries impose quite specific quality standards. For example, the US authorities require that the concentrations in milk of the following six antibiotics do not exceed quite specific values: penicillin, 5 ppb; ampicillin, 10 ppb; amoxicillin, 10 ppb; cloxacillin, 10 ppb; cephapirin, 20 ppb, ceftiofur, 50 ppb. The European Union imposes quality standards as follows: penicillin, 4 ppb; amoxicillin, 4 ppb; ampicillin, 4 ppb; cloxacillin, 30 ppb; dicloxacillin, 30 ppb; oxacillin, 30 ppb; cephapirin, 10 ppb, ceftiofur, 100 ppb; cefquinone 20 ppb; nafcillin 30 ppb; cefazoline, 50 ppb.

It may thus be advantageous to have access to a test which would allow most of the antibiotics to be detected. Moreover, in the dairy industry, it may be considered that, in the absence of a test which has all the characteristics of speed, sensitivity and simplicity, a test which would allow the best combination of these three parameters, even if they are not totally covered, would be advantageous.

Various types of tests have already been proposed for the detection of antibiotics containing a β-lactam ring in a biological fluid.

These tests generally make use of detection methods which employ a recognition agent (receptor or antibody), which recognizes specifically the antibiotic or an analogue of this antibiotic, and a labelling agent (radioelement, enzyme, fluorescent agent, etc.), these agents being referred to hereinafter as detection reagents. Depending on the elements chosen, use is made of the terms radioimmunoassay (RIA), radioreceptor assay (RRA), enzyme immunoassay (EIA), etc. In their general principle, these tests employ the minimum combination of the two abovementioned elements (detection reagents) which will make it possible to obtain a result whose value is an indication of the quantity of analyte present.

It should be noted that, depending on the detection method selected, the labelling agent can be coupled alternatively to the recognition agent or to the antibiotic or to an analogue substance of the antibiotic in terms of its recognition by the recognition agent. There are also processes in which the recognition agent or the antibiotic or the analogue substance of the antibiotic contains, intrinsically, the labelling agent (for example, a radiolabelled analyte).

For dairy products, the analyte detection tests which are most widely described relate to the detection of antibiotics.

U.S. Pat. No. 4,239,852 describes a microbiological process for the detection in milk of antibiotics having a β-lactam ring. According to this process, the sample of milk is incubated firstly in the presence of cell parts of a microorganism which is highly sensitive to antibiotics, and especially *Bacillus stearothermophilus*, and secondly in the presence of an antibiotic which is labelled ("tagged") with a radioactive element or with an enzyme. The incubation is conducted under conditions which allow antibiotics, if present in the sample, and the labelled antibiotic to bind to the cell parts.

Following incubation, the cell parts are separated from the mixture and then washed. Subsequently, the quantity of labelled antibiotic bound to the cell parts is determined and is compared with a standard. The quantity of labelled antibiotic bound to the cell parts is inversely proportional to the concentration of antibiotic present in the milk sample analysed.

This process requires fairly delicate handling, especially at the stage of separating the cell parts from the mixture. In addition, in its most sensitive version, which allows the detection of Penicillin G up to 0.01 I.U./ml and even up to 0.001 I.U./ml in milk, this process uses an antibiotic labelled with a radioactive element ($^{14}C$ or $^{125}I$). In this case, the determination of the quantity of antibiotic present or otherwise in the milk necessitates the use of a special instrument such as a scintillation counter, for example. In addition, handling radioactive products even in very small quantities is not completely free of risk for the person conducting the analysis.

European Patent Application 593 112 describes another method permitting the detection of antibiotics in milk. This method uses a protein isolated from an antibiotic-sensitive microorganism, such as *Bacillus stearothermophilus*. This protein is additionally labelled with an enzyme such as a peroxidase.

The test proceeds as follows: a sample of milk is incubated in a tube in the presence of the labelled protein; after incubation, the milk is transferred to a second tube on whose walls a reference antibiotic has been immobilized; a second incubation is carried out, and then the contents of the tube are removed; the walls of this second tube are washed three times with a wash solution, which is itself removed, and then the residues present in the second tube are transferred to a piece of absorbent paper; a colouring substrate is then added to the second tube, which is incubated once again, and then a solution which retards the development of the colour is added; the coloration of the tube is compared with the coloration of an identical test carried out in parallel on a standard sample of antibiotic. The quantity of labelled protein immobilized on the support, and therefore the intensity of the coloration, is inversely proportional to the quantity of antibiotic present in the milk sample analysed.

According to Example 1 of this patent application, this test makes it possible to detect penicillin G down to concentrations of the order of 5 ppb and makes it possible to detect amoxicillin (5 ppb), ampicillin (10 ppb), cephapirin (5 ppb) and ceftiofur (5 ppb). This test does not allow the detection of penicillin, amoxicillin and ampicillin up to the levels imposed by European Regulations and, on the other hand, this test is rather complex; it does not entirely fulfil the criteria of sensitivity and of simplicity sought in the context of the present invention.

However, the test is very tiresome to carry out, especially by unskilled personnel. Indeed, this test comprises numerous steps, including steps of transferring liquid and residues from one vessel to another, and a number of rinsing steps. Given the number and the type of steps required in this test, obtaining a reliable result depends heavily on the experimental know-how of the operative.

In addition, interpreting the result requires two tests to be carried out in parallel, thereby multiplying and further complicating the operations.

Other types of enzymatic processes have also been disclosed, which make it possible to determine low concentrations of antibiotics in milk (J. M. Frere et al., Antimicrobial Agents and Chemotherapy, 18(4), 506-510 (1980), and patents EP 85 667 and EP 468 946), which are based on the use of a specific enzyme, namely soluble exocellular D-alanyl-D-alanine carboxypeptidase, which is produced by Actinomadura R39 (designated "enzyme R39" hereinafter). Enzyme R39 possesses a specific activity of hydrolysing the D-alanyl-D-alanine groups of various peptides and is also capable of hydrolysing certain thioesters.

In addition, enzyme R39 reacts with antibiotics having a β-lactam ring to form very rapidly an equimolar enzyme-antibiotic complex which is inactive and substantially irreversible.

In the most recent version of this test (EP 468 946) a predetermined volume of a sample of the liquid to be examined is incubated with a predetermined quantity of enzyme R39 under conditions which allow the β-lactam antibiotic which may be present in the sample to react with the enzyme to form an equimolar enzyme-antibiotic complex which is inactive and substantially irreversible.

Subsequently, a predetermined quantity of thioester-type substrate is incubated with the product obtained in the first stage under conditions which allow the substrate to be hydrolysed by the residual enzyme R39 which has not been complexed with the antibiotic in the course of the first incubation. The quantity of mercaptoalkanoic acid thus formed is then determined by calorimetric assay with the aid of a reagent capable of producing a coloration by reaction with the free SH group of the mercaptoalkanoic acid. The intensity of the coloration is compared with a standard established beforehand from samples containing known quantities of antibiotics. Quantitative determination can be carried out by measurement in a spectrophotometer; in the case of milk, it may be necessary to clarify the sample beforehand.

According to the embodiments of patent EP 468,946, this process makes it possible to determine, in milk, 10 ppb of penicillin G for a total incubation time of 5 minutes and about 2.5 ppb of penicillin G for a total incubation time of 15 minutes.

Given the criteria of speed, simplicity and sensitivity required for the methods for detecting antibiotics in food products, the Applicant set itself the aim of investigating novel, even more effective methods for detecting antibiotics in a biological fluid. In particular, the Applicant set itself the aim of investigating methods for detecting, in a single test, most of the antibiotics whose content is regulated by the European and US authorities. Furthermore, the methods investigated should make it possible to obtain this result in a limited number of steps, which can preferably be carried out by unqualified personnel. The Applicant also investigated methods for achieving these aims with an incubation time which is shorter than that in the existing processes.

The Applicant has just discovered novel processes for detecting antibiotics containing a lactam ring in a biological fluid, which allow these objectives to be achieved in a noteworthy manner.

Accordingly, the present invention relates to novel processes for detecting antibiotics containing a β-lactam ring in a biological fluid, comprising the following steps
a) placing a determined volume of the said biological fluid in contact with an amount of recognition agent and incubating the mixture thus obtained under conditions which allow the complexation of the antibiotics, which may be present in the said biological fluid, with the recognition agent,
b) placing the mixture obtained in step a) in contact with at least one reference antibiotic immobilized on a support, under conditions which allow the complexation of the reference antibiotic with the amount of recognition agent which has not reacted in step a), and
c) determining the amount of recognition agent bound to the support, characterized in that the recognition agent comprises a receptor which is sensitive to the antibiotics containing a β-lactam ring obtained from *Bacillus licheniformis*.

FIG. 1 illustrates a type of support which can be used according to the present invention, which is in the form of a test device comprising a solid support (1) on which membranes (2), (3) and (4) are attached. FIG. 1a is a front view and FIG. 1b is a view in longitudinal cross section of the test device.

The exceptional performance of the process according to the present invention is based on the use of a specific recognition agent, which comprises a receptor which is sensitive to the antibiotics containing a β-lactam ring obtained from *Bacillus licheniformis*, i.e. the BlaR protein whose isolation and peptide sequence are described in Y. Zhu et al., J. Bacteriol., 1137-1141, (1990), or the BlaR-CTD polypeptide, which is the carboxy terminal region of BlaR, whose isolation and peptide sequence are described in B. Joris et al., FEMS Microbiology Letters, 107-114, (1990).

The use of the BlaR or BlaR-CDT receptors according to the present invention for the detection of antibiotics containing β-lactam rings has appreciable advantages over the recognition agents used hitherto. The reason for this is that the BlaR and BlaR-CDT receptors are capable of very rapidly complexing a very large number of antibiotics, and of doing so in a shorter incubation time than that required for the known recognition agents such as, for example, the receptors obtained from *Bacillus stearothermophilus*.

As examples of antibiotics which can be detected by means of the processes according to the present invention, mention may be made of the following antibiotics: benzylpenicillin (or penicillin G), ampicillin, amoxicillin, carbenicillin, methylcillin, cloxacillin, 6-APA, monolactam, aztreonam, mecillinam, cephalexine, cephaloglycine, cephaloridine, nitrocephine, cefatoxime, cefuoroxime, ceftiofur, cephapyrine, 7-ACA. More particularly, the processes according to the present invention make it possible to detect all the antibiotics controlled by the US and European authorities, down to the limit thresholds tolerated.

The processes according to the invention allow the detection of antibiotics containing a β-lacatam ring in biological fluids such as milk, urine, blood, serum, saliva, meat extracts, fermentation liquids or buffered aqueous media.

According to a preferred embodiment of the processes of the invention, the recognition agent is used in a form coupled to a labelling agent. This labelling agent can be of diverse nature. The labelling agent can be of particulate type, such as metallic colloidal particles (platinum, gold, silver, etc.), colloidal particles of selenium, carbon, sulphur or tellurium, or alternatively colloidal particles of coloured synthetic latexes. The labelling agent can also be a fluorescent substance, such as activated fluorescein (available from Boeringher-Mannheim Biochemica), fluorescein isocyanate, rhodamine tetramethylisocyanate or any other fluorescent substance known to those skilled in the art. The labelling agent can also be enzymatic, for example a β-lactamase, a peroxidase, a phosphatase, etc. In this case, the BlaR or BlaR-CTD receptors are chemically or genetically coupled to this enzymatic labelling agent to form a fusion protein.

The recognition agent can be coupled with the labelling agent according to the conventional methods known to those skilled in the art. The recognition agent can be bound either directly to the labelling agent, or via the formation of an intermediate complex. Coupling between the recognition agent and the labelling agent can take place at different times during the implementation of the processes of the invention. According to a first embodiment, the coupling between the recognition agent and the labelling agent takes place before the recognition agent is placed in contact with the biological fluid to be analyzed. According to other embodiments of the processes of the invention, the coupling between the recognition agent and the labelling agent can take place when or after the recognition agent is placed in contact with the sample of biological fluid. Preferably, the labelling of the recognition agent takes place before the recognition agent is placed in contact with the sample to be analyzed.

The first step a) of the processes according to the invention consists in placing a determined volume of the biological fluid in contact with an amount of recognition agent and incubating the mixture obtained under conditions which allow complexing of the antibiotics, which may be present in the biological fluid, with the recognition agent.

The biological fluid can be incubated with the BlaR or BlaR-CTD receptor within a temperature range of between 4 and 60° C. Preferably, this temperature is about 47° C. An increase in the incubation temperature will have the effect of decreasing its duration, and vice versa. It is thus always possible to reduce the duration of the process by increasing the temperature.

In the second step b) of the process according to the present invention, the mixture obtained in step a) is placed in contact with at least one reference antibiotic immobilized on a support.

The supports which can be used according to the present invention may be of very varied types. They can be solid supports such as tubes, plates or rods coated with a reference antibiotic preparation. It can be a test device in the form of a solid support on which membranes are bound, one or more capture substance being placed in a determined detection zone. They can be supports in the form of magnetic or non-magnetic beads (agarose, polystyrene, etc.), capable of forming a gel and on which the reference antibiotic is immobilized.

The reference antibiotic can be immobilized on the support by the methods known to those skilled in the art, for example by covalent or non-covalent absorption onto the support, optionally via a spacer.

According to a specific embodiment of the invention, steps a) and b) can take place simultaneously.

Step c) of the process according to the present invention consists in determining the receptors which are attached to the support on which the reference antibiotic is immobilized. The method used for this determination is directly associated with the type of labelling agent used. If the labelling agent is enzymatic, the determination step will involve a reaction specific for this enzyme, which is associated, for example, with the production of a given coloration. If the labelling agent is fluorescent, the determination will be carried out by simply measuring the fluorescence of the support. In the case of metal particles or coloured latices, the presence of receptors attached to the support is reflected by a coloration whose intensity is directly proportional to the number of receptors attached to the support. Irrespective of the type of labelling agent used, the intensity of the signal detected is inversely proportional to the amount of antibiotic present in the sample analyzed.

The present invention also relates to test kits for detecting antibiotics in a biological fluid, comprising at least one recognition agent which comprises a receptor which is sensitive to the antibiotics containing a β-lactam ring obtained from *Bacillus licheniformis*, and at least one reference antibiotic immobilized on a support.

The examples which follow illustrate various aspects and methods for implementing the present invention, without, however, limiting its scope.

EXAMPLE 1

Determination of Antibiotics Containing a β-Lactam Ring in Milk

This example illustrates the detection in milk of antibiotics containing a β-lactam ring, which are controlled by the health authorities. The test described in this example uses the BlaR-CTD receptor coupled to gold beads which serve as labelling agents, and uses a support in the form of a test device comprising a solid support to which membranes are attached.

1.1. Coupling of BlaR-CTD to Gold Beads 1.1.1. Biotinylation of BlaR-CTD 3.79 ml of a solution of recognition agent BlaR-CTD having a concentration of 6.6 mg/ml are taken up in a sodium phosphate buffer, 20 mM pH 7. To this solution of BlaR-CTD are then added 41.71 ml of bicarbonate buffer (0.1 M sodium bicarbonate, pH 9) and 2 ml of a solution of N-hydroxysuccinimide 6-(biotinamido)caproic ester containing 2.23 mg/ml likewise of bicarbonate buffer. This solution is stirred gently on a LABINCO stirrer for tubes on a rotary axis (available from VEL, Belgium) at a rate of 2 revolutions/minute for 2 hours at ambient temperature and away from light. 2.5 ml of a solution of Tris buffer, 1 M pH 8 are incubated with the reaction mixture under the same conditions for 30 minutes. The solution thus obtained is dialysed against HNM buffer (Hepes 100 mM, pH 8, NaCl 100 mM, $MgCl_2$ 50 mM) for 24 hours. In this way a biotinylated BlaR-CTD solution is obtained which is diluted in HNM-BSA buffer (Hepes 500 mM, pH 8, NaCl 500 mM, $MgCl_2$ 250 mM, BSA 10 mg/ml) to a concentration of 250 mg of biotinylated BlaR-CTD per ml of buffer. This solution is stored at −20° C.

1.1.2. Labelling Agent.

As the labelling agent use is made of particles of gold having a diameter of 40 nm on which a goat antibiotin antibody has been deposited in the form of suspensions in a 2 mM aqueous sodium tetraborate solution, with a pH of 7.2, stabilized by 0.1% of sodium azide (available from British Biocell (Ref. GAB40)). The optical density of these suspensions at 520 nm is approximately 10 and the protein concentration is approximately 24 mg/ml.

1.1.3. Coupling the Biotinylated BlaR-CTD to Gold Particles.

The biotinylated BlaR-CTD solution prepared in Example 3.1.1 is diluted 114.7 times with the HNM-BSA buffer (Hepes 500 mM, pH 8, NaCl 500 mM, $MgCl_2$ 250 mM, BSA 10 mg/ml). At room temperature, 22.5 parts by volume of this dilute biotinylated BlaR-CTD solution, 7.5 parts by volume of HNM-BSA buffer, 9.27 parts by volume of the gold particle suspension used to label the biotinylated BlaR-CTD and 6 parts by volume of reference gold particle suspension are mixed (see Example 3.1.4 below).

1.1.4. Independent Reference.

In this test, use is also made of a reference substance which supplies a band whose intensity enables rapid quantification of the antibiotic present in the sample.

For this purpose use is made of 40 nm particles of gold on which a goat anti-rabbit immunoglobulin antibody has been deposited. These particles are available from British Biocell (Ref. GAR40) in the form of suspensions in 2 mM aqueous sodium tetraborate solution, with a pH of 7.2, stabilized by 0.1% sodium azide. The optical density of these suspensions at 520 nm is approximately 3 and the protein concentration is approximately 6 mg/ml.

1.2. Test Device

The test device used comprises a solid support (1) which has the first and second end, to which are attached, successively, starting from the first end,
- a membrane (2) for purifying the fluid analyzed,
- a membrane (3) on which two capture substances (reference antibiotic and substance capable of binding the independent reference) are immobilized, and
- an absorbent membrane (4).

1.2.1. Assembling Assay Devices.

Cards having a size of 300×76.2 mm are first of all assembled using a laminator of the Clamshell laminator type (available from BioDot, Inc.) in accordance with the following method:

A plastic support rectangle of type ArCare 8565 (available from Adhesive Research) is cut out, measuring 300×76.2 mm (solid support (1)). Subsequently, a rectangle of Leukosorb LK4 membrane (available from Pall Gelman Sciences), measuring 300×20 mm (membrane (2)), a rectangle of Hi-Flow SX membrane (available from Millipore), measuring 300×25 mm (membrane (3)), a rectangle of 3 mm cellulose membrane (available from Whatman), measuring 300×40 mm (membrane (4)).

In succession, the membranes (2) and (4), then (3) are placed in a specific location of the lower mould of the laminator. The solid support (1), covered with adhesive, is for its part held in the cover of the apparatus, with the adhesive face exposed to the air. The membranes placed in the lower mould are brought into contact with the adhesive support by closing the laminator; the membranes are held exactly in place by means of air suction from a vacuum pump. When the vacuum is broken, a card is recovered which consists of the solid support (1) with, fixed thereon, the membranes (2), (3) and (4).

The following solutions are then deposited on the membrane (3): proximal side: first capture substance; band No. 1; distal side: second capture substance; band No. 2. These capture substances are deposited using a "Dispenser" of X-Y Platform Biojet Quanti-3000 type from Bio Dot Inc.

The deposited solutions are immediately evaporated by placing the whole of the card for one minute under hot forced air at 60° C.

The cards obtained after assembly are cut into strips with the aid of a guillotine-type apparatus or with the aid of a rotary apparatus (available from BioDot, Kinematic or Akzo). The end strips are removed, with the other strips being ready for use.

FIG. 1 illustrates such an assay device.

To preserve them, the assay devices are placed in an opaque, hermetically sealed container in the presence of a dessicant (Silgelac, France).

1.2.2. First Capture Substance. Reference Antibiotic.

8 ml of a solution containing 213 mg of human gamma globulin (G4386, Sigma) and 8.6 mg of 2-iminothiolane hydrochloride (Aldrich, 33056-6) in sodium carbonate buffer (100 mM, pH 9) are incubated at 25° C. for one hour.

In addition, 20 ml of a solution containing 119.8 mg of cephalosporin C and 54 mg of sulphosuccinimidyl 4-(N-maleimidomethyl)cyclohexane-1-carboxylate (sSMCC, 22322 Pierce) in sodium carbonate buffer (100 mM, pH 9) are incubated at 25° C. for one hour.

The two solutions prepared above are then mixed. The pH of the resulting solution is adjusted to 7.1 by adding 3 ml of $NaH_2PO_4$ 500 mM, and the solution is incubated at 25° C. for two hours. The mixture obtained after incubation is dialysed three times against 1 liter of sodium phosphate buffer (10 mM, pH 7.5). The resulting solution is filtered through a 0.22 mm filter, then divided into aliquots and frozen at −20° C. until use.

At the time of use, the aliquots are thawed and a food colorant is added to them before they are deposited on the membrane, so as to indicate at any moment the exact position of the deposit and the quality of the trace.

The first capture substance makes it possible to fix BlaR-CTD coupled to the gold particles in excess with respect to the quantity of antibiotic present in the sample.

1.2.3. Second Capture Substance. Substance Capable of Fixing the Independent Reference.

For the second capture substance use is made of a rabbit immunoglobulin solution (Sigma I 5006) having an immunoglobulin concentration of 0.5 mg/ml in a 10 mM sodium phosphate, pH 7.5, human gamma globulin 5 mg/ml buffer. This second capture substance stops the reference as the liquid migrates over the assay device.

1.3. Determination of the Antibiotics in Milk

1.3.1. 3-Minute Test—Rapid Test 7 samples of fresh milk containing 0; 1; 2; 3; 4; 5 and 6 ppb of penicillin G, respectively, are prepared. Each of these solutions is then analyzed in the following way:

A 200 μl aliquot sample of milk and 45.27 μl of solution prepared in Example 1.1.3 are taken and placed in a glass flask. This mixture is incubated for 1 minute at 47° C. A test device is taken and placed vertically in the glass flask such that the first end of the test device is in contact with the mixture and such that the second end rests on the wall of the glass flask. The mixture is left to migrate on the test device, while incubating the assembly for 2 minutes at 47° C.

Table 1 below summarizes the results obtained for the 7 samples tested. An intensity value ranging from 0 to 10 is attributed to the bands detected, the value 10 being given to the most intense band and the value 0 being given to the least intense band. According to this scale, a value of 6 is assigned to the reference band. The intensity of the signal observed in the first band is inversely proportional to the amount of penicillin G present in the sample.

TABLE 1

| Penicillin G | Intensity | |
|---|---|---|
| (ppb) | 1st band | 2nd band |
| 0 | 10 | 6 |
| 1 | 9 | 6 |
| 2 | 9 | 6 |
| 3 | 4 | 6 |
| 4 | 0 | 6 |
| 5 | 0 | 6 |
| 6 | 0 | 6 |

In this example, when the first band has an intesity less than that of the second band, the test is considered as being positive. The results given in Table 1 show that this test allows the detection of less than 4 ppb of penicillin G in a sample of milk in 3 minutes.

Tests were also carried out with other antibiotics containing a β-lactam ring under the same conditions. This test carried out in 3 minutes allows the detection of amoxycillin down to 5 ppb, ampicillin down to 5 ppb, cloxacillin to less than 10 ppb, dicloxacillin to less than 20 ppb, oxacillin to less than 20 ppb and cephapirin down to 20 ppb in a sample of milk.

1.3.2. 5-Minute Test 6 samples of fresh milk containing 0; 2; 4; 6; 8 and 10 ppb of cloxacillin, respectively, are prepared. Each of these solutions is then analyzed in the following way.

A 200 µl aliquot sample of milk and 45.27 µl of solution prepared in Example 1.1.3 are taken and placed in a glass flask. This mixture is incubated for 3 minutes at 47° C. A test device is taken and placed vertically in the glass flask such that the first end of the test device is in contact with the mixture and such that the second end rests on the wall of the glass flask. The mixture is left to migrate on the test device, while incubating the assembly for 2 minutes at 47° C.

Table 2 below summarizes the results obtained for the 6 samples tested. An intensity value ranging from 0 to 10 is attributed to the bands detected, the value 10 being given to the most intense band and the value 0 being given to the least intense band. According to this scale, a value of 6 is assigned to the reference band. The intensity of the signal observed in the first band is inversely proportional to the amount of cloxacillin present in the sample.

TABLE 2

| Cloxacillin | Intensity | |
|---|---|---|
| (ppb) | 1st band | 2nd band |
| 0 | 10 | 6 |
| 2 | 6 | 6 |
| 4 | 5 | 6 |
| 6 | 3 | 6 |
| 8 | 3 | 6 |
| 10 | 3 | 6 |

In this example, when the first band has an intesity less than that of the second band, the test is considered as being positive. The results given in Table 2 show that this test allows the detection of less than 4 ppb of cloxacillin in a sample of milk in 5 minutes.

Tests were also carried out with other antibiotics containing a β-lactam ring under the same conditions. This test carried out in 5 minutes allows the detection of penicillin G down to 3 ppb, amoxycillin down to 4 ppb, ampicillin down to 4 ppb, dicloxacillin down to 8 ppb, oxacillin down to 8 ppb, cephapirin down to 16 ppb, ceftiofur down to 100 ppb, cefguinone to less than 20 ppb, nafcillin down to 20 ppb and cefazoline down to 60 ppb in a sample of milk.

This test is particularly suitable as a sorting test before the milk wagons are emptied into silos.

1.3.3. 9-Minute Test 6 samples of fresh milk containing 0; 4; 6; 8; 10 and 12 ppb of cephapirin, respectively, are prepared. Each of these solutions is then analyzed in the following way.

A 200 µl aliquot sample of milk and 45.27 µl of solution prepared in Example 1.1.3 are taken and placed in a glass flask. This mixture is incubated for 7 minutes at 47° C. A test device is taken and placed vertically in the glass flask such that the first end of the test device is in contact with the mixture and such that the second end rests on the wall of the glass flask. The mixture is left to migrate on the test device, while incubating the assembly for 2 minutes at 47° C.

Table 3 below summarizes the results obtained for the 6 samples tested. An intensity value ranging from 0 to 10 is attributed to the bands detected, the value 10 being given to the most intense band and the value 0 being given to the least intense band. According to this scale, a value of 6 is assigned to the reference band. The intensity of the signal observed in the first band is inversely proportional to the amount of cephapirin present in the sample.

TABLE 3

| Cephapirin | Intensity | |
|---|---|---|
| (ppb) | 1st band | 2nd band |
| 0 | 10 | 6 |
| 4 | 6 | 6 |
| 6 | 5 | 6 |
| 8 | 4 | 6 |
| 10 | 3 | 6 |
| 12 | 3 | 6 |

In this example, when the first band has an intesity less than that of the second band, the test is considered as being positive. The results given in Table 3 show that this test allows the detection down to 6 ppb of cephapirin in a sample of milk in 9 minutes.

Tests were also carried out with other antibiotics containing a β-lactam ring under the same conditions. This test carried out in 9 minutes allows the detection of penicillin G down to 3 ppb, amoxycillin down to 4 ppb, ampicillin down to 4 ppb, cloxacillin down to 4 ppb, dicloxacillin to less than 8 ppb, oxacillin to less than 8 ppb, ceftiofur down to 80 ppb, cefquinone to less than 20 ppb, nafcillin to less than 20 ppb and cefazoline down to 45 ppb in a sample of milk.

This test carried out in 9 minutes thus allows detection of all the antibiotics currently controlled by the European authorities, down to the legal limits imposed by these authorities.

1.3.4. 20-Minute Test 6 samples of fresh milk containing 0; 20; 30; 40; 50 and 60 ppb of ceftiofur, respectively, are prepared. Each of these solutions is then analyzed in the following way.

A 200 µl aliquot sample of milk and 45.27 µl of solution prepared in Example 1.1.3 are taken and placed in a glass flask. This mixture is incubated for 18 minutes at 47° C. A test device is taken and placed vertically in the glass flask such that the first end of the test device is in contact with the mixture and such that the second end rests on the wall of the glass flask. The mixture is left to migrate on the test device, while incubating the assembly for 2 minutes at 47° C.

Table 4 below summarizes the results obtained for the 6 samples tested. An intensity value ranging from 0 to 10 is attributed to the bands detected, the value 10 being given to the most intense band and the value 0 being given to the least intense band. According to this scale, a value of 6 is assigned to the reference band. The intensity of the signal observed in the first band is inversely proportional to the amount of ceftiofur present in the sample.

TABLE 4

| Ceftiofur | Intensity | |
|---|---|---|
| (ppb) | 1st band | 2nd band |
| 0 | 10 | 6 |
| 20 | 6 | 6 |
| 30 | 5 | 6 |
| 40 | 4 | 6 |
| 50 | 3 | 6 |
| 60 | 3 | 6 |

In this example, when the first band has an intensity less than that of the second band, the test is considered as being positive. The results given in Table 4 show that this test allows the detection of ceftiofur down to 30 ppb in a sample of milk in 20 minutes.

This test over 20 minutes thus allows detection, in a single test, of all the antibiotics currently controlled by the European and US authorities, down to the legal limits imposed by these authorities.

EXAMPLE 2

Determination of 6 Antibiotics in Milk

This example illustrates the detection in milk of the 6 antibiotics containing a β-lactam ring which are controlled by the US authorities. The test described in this example uses the BlaR-CTD receptor in the form of a fusion protein with β-lacatamase and uses a support in the form of magnetic beads.

2.1 BlaR-CTD-β-Lactamase Fusion Protein.

The BlaR-CTD-β-lactamase fusion protein is obtained by genetic coupling between the BlaR-CTD receptor (B. Joris et al., FEMS Microbiology Letters, 107-114, 1990) and Zn β-lactamase from *Bacillus cereus* (M. Hussain et al., 1985, J. Bact., 164:1, 223-229, 1985).

The coupling is carried out in the following way:

2.1.1. Construction of the plasmid: a 1/1 coupling was carried out between the genes of the BlaR-CTD polypeptide and β-lactamase: the gene coding for β-lactamase was introduced in phase and behind the BlaR-CTD gene. The plasmid bearing the genetic fusion shows resistance to kanamycin. The fusion protein is referred to below as Fus 1.

2.1.2. Production:
Strain: the plasmid bearing the fused genes was introduced into *E. Coli*. The clones bearing the recombinant plasmid are selected on LB+Km (50 µg/ml).
Selection: labelling of the cell extract with a radioactive antibiotic, followed by electrophoresis on denaturing polyacrylamide gel shows that most of the protein is produced in the form of a fusion protein whose molecular mass is about 50,000. However, a post-translational proteolysis appears to dissociate a very small percentage (2%) of these molecules into two separate activities.

Culturing: 500 ml of LB+Km medium (50 µg/ml) are inoculated using recombinant cells stored at −70° C. The preculture is incubated at 37° C. and stirred overnight at 225 rpm. 18 liters of LB+Km medium (50 µg/ml) are inoculated with 500 ml of this preculture, the optical density of which at 600 nm is 4. The 18-liter culture is stopped when the optical density reaches a value of 6.

2.1.3. Extraction: immediately after stopping the culturing, the cells are filtered and then centrifuged. The supernatant from the cell pellet lysed in a disintegrator is kept. It contains the fusion protein FUSi.

2.1.4. Purification:
Buffers used:
Buffer A: 20 mM pH 8.0 Tris, 10% ethyleneglycol, 50 µm DTT;
Buffer B: buffer A+1M NACl.

The fusion protein is partially purified by ionic chromatography and on molecular sieves. After depositing the extract and washing on a QSFF column (Pharmacia, Upsala) in buffer A, FUS1 is eluted with a linear gradient of buffer B. The active fractions (±0.25 M NaCl) are then combined and deposited on G-100 molecular sieves (Pharmacia, Upsala); they are eluted with buffer A. The average specific activity of the batch recovered is estimated at 30%.

2.1.5. Inhibition of β-lactamase: the fusion protein (9/10 volume) is incubated with 50 mM EDTA (1/10 volume) for 45 minutes at 37° C. The inhibition is checked using nitrocefine in 10 mM pH 6.0 cacodylate buffer. In the presence or absence of Zn, the signal should be positive or negative, respectively. After inhibition, the effective concentration, measured on the basis of the β-lactamase activity, is 7.74 pmol/µl.

2.2 Solid support: magnetic beads—cephalosporin C (reference antibiotic).

BioMag 4100 particles (available from DRG Instrument GmbH, Marburg, Germany, under the reference AM 4100 B) are used, the $NH_2$ ends of which have been activated with glutaraldehyde in the following way:
one volume of initial solution of BioMag 4100 particles is rinsed 4 times with 5 volumes of 0.01M pH 6.0 pyridine buffer. The particles are taken up in 2.5 volumes of glutaraldehyde at 5% in pyridine buffer and are agitated by rotation for 3 hours at room temperature. They are then rinsed 10 times with 2 volumes of 0.01 M pH 7.0 Kpi buffer. The particles are then resuspended in 1 volume of 0.1 M cephalosporin C in Kpi buffer and are agitated by rotation overnight at +4° C. The final rinsing is carried out until the cephalasporin C has been completely removed from the 0.1 M pH 7.0 Kpi buffer.

2.3. Determination of the 6 Antibiotics Penicillin G, Ampicillin, Amoxicillin, Cloxacillin, Cephapirin and Certiofur in Milk.

2.3.1 Solutions Used:
solution 1: 700 picomol of fusion protein lyophilized in 100 mM, pH 8 Tris, 1 mg/ml BSA, 50 mM EDTA, 50 µm DTT are rehydrated with 5 ml of Milli-Q water; 50 µl of this solution are required to carry out a measurement.
solution 2: 2 ml of BioMag-cephalosporin C particles prepared in Example 1.2 in 100% isopropanol; 20 µl are required to carry out a measurement.
solution 3: 10 mM, pH 6 cacodylate buffer, 1 M NaCl lyophilized and rehydrated with 500 ml of Milli-Q water.
solution 4: 400 ml of 10 mM nitrocefine in DMF are diluted to 40 ml in solution 3; 400 µl are required for a detection.

2.3.2. Detection Process:

50 µl of solution 1 are placed in the presence of 500 ml of doped milk samples and incubated at 47° C. for 2 minutes. 20 µl of solution 2 are suspended in the milk, which is reincubated for 2 minutes at 47° C. The particles are attracted against the wall of the container using a paramagnetic magnet while the supernatant is emptied from the tube. The particles are rinsed twice with solution 3, performing the same process with the magnet. Finally, 400 µl of solution 4 are incubated in the presence of the particles for 3 minutes at 47° C. The absorbance of the residual solution at 482 nm is then measured relative to the nitrocefine solution.

This process allows detection of the 6 antibiotics given in the US Regulations at concentrations below the standards imposed by the authorities, i.e. penicillin at 5 ppb, ampicillin at 10 ppb, amoxicillin at 10 ppb, cloxacillin at 10 ppb, cephapirin at 20 ppb and ceftiofur at 50 ppb.

EXAMPLE 3

Determination of 3 Antibiotics (Penicillin G, Cloxacillin, Ceftiofur) in Milk

This example illustrates the detection in milk of 3 antibiotics containing a β-lactam ring which are controlled by the health authorities. The test described in this example uses the BlaR-CTD receptor in the form of two fusion proteins with alkaline phosphatase and peroxidase, respectively, and uses a support in the form of a microplate.

3.1. BlaR-CTD-Alkaline Phosphatase Fusion Protein.

The BlaR-CTD-alkaline phosphatase fusion protein is obtained by chemical coupling between the BlaR-CTD receptor (B. Joris et al., FEMS Microbiology Letters, 107-114 (1990)) and the activated alkaline phosphatase available from Boehringer-Mannheim Biochemica under the reference 1464752.

The coupling was carried out in the following way:

3.1.1. Conjugation: BlaR-CTD and alkaline phosphatase are dialysed in 100 mM sodium carbonate/bicarbonate buffer at pH 9.8. 15 nonomol of BlaR-CTD are incubated in the presence of 100 µl of activated alkaline phosphatase (20 mg/ml) for 2 hours at 25° C.

3.1.2. Stopping the reaction: 40 µl of a 2 mM, pH 8 trithanolamine solution are added, followed by 50 µl of a 200 mM sodium borohydride solution. The mixture is incubated for 30 min at +4° C. 25 µl of 2 mM, pH 8 triethanolamine solution are then added, after which the mixture is reincubated for 2 hours at +4° C.

3.1.3. Stabilization of the coupling: 10 µl of 1M, pH 7.0 glycine solution are added.

3.1.4. Transfer into the storage buffer: the reaction mixture (about 300 µl) is dialysed for three times 8 hours against 0.5 liter of 50 mM, pH 7.6 triethanolamine buffer, 150 mM NaCl, 1 mM $MgCl_2$, 0.5 mM $ZnCl_2$, 10 mM glycine at +4° C.

3.1.5. Final titre: the final titre of the coupling is about 50 pmol of active BlaR-CTD per µl of solution.

3.2. BlaR-CTD-Peroxidase Fusion Protein

The BlaR-CTD-peroxidase fusion protein is obtained by chemical coupling between the BlaR-CTD receptor (B. Joris et al., FEMS Microbiology Letters, 107-114, (1990)) and the activated peroxidase available from Boehringer-Mannheim Biochemica under the reference 1428861.

The coupling is carried out in the following way:

3.2.1. Conjugation: BlaR-CTD and peroxidase are dialysed in 100 mM, pH 9.8 sodium carbonate/bicarbonate buffer. 40 nanomol of BlaR-CTD are incubated in the presence of 100 µl of activated peroxidase (16 mg/ml) for 2 hours at 25° C.

3.2.2 Stopping the reaction: 40 µl of 2 mM, pH 8 triethanolamine solution are added, followed by 50 µl of 200 mM sodium borohydride solution. The mixture is incubated for 30 min at +4° C. 25 µl of 2 mM, pH 8 triethanolamine solution are then added, after which the mixture is reincubated for 2 hours at +4° C.

3.2.3. Stabilization of the coupling: 10 µl of 1M, pH 7.0 glycine solution are added.

3.2.4. Transfer into the storage buffer: the reaction mixture (about 400 µl) is dialysed for three times 8 hours against 0.5 liter of 10 mM, pH 7.5 potassium phosphate buffer, 200 mM NaCl, 10 mM glycine at +4° C.

3.2.5. Final titre: the final titre of the coupling is about 100 pmol of active BlaR-CTD per µl of solution.

3.3. Solid support: microplate-cephalosporin C.

3.3.1. Preparation of the Reference Antibiotic Solution.

8 ml of a solution containing 213 mg of human gamma-globuliin (G4386, Sigma) and 8.6 mg of 2-iminothiolane hydrochloride (Aldrich, 33056-6) in sodium carbonate buffer (100 mM, pH 9) are incubated for one hour at 25° C.

Separately, 20 ml of a solution containing 119.8 mg of cephalosporin-C and 54 mg of sulphosuccinimidyl 4-(N-maleimidomethyl)cyclohexane-1-carboxylate (sSMCC, 22322 Pierce) in sodium carbonate buffer (100 mM, pH 9) are incubated for one hour at 25° C.

The two solutions prepared above are then mixed together. The pH of the resulting solution is adjusted to 7.1 by adding 3 ml of 500 mM $NaH_2PO_4$ and the mixture is incubated for 2 hours at 25° C. The mixture obtained after incubation is dialysed three times against 1 liter of sodium phosphate buffer (10 mM, pH 7.5). The resulting solution is filtered through a 0.22 µm filter.

3.3.2. Coating of the Microplates with the Reference Antibiotic.

Polystyrene microplates with high protein adsorption, of the brand name NUNK (Immuno Plate: Maxisorp type) or of the brand name GREINER (microlon 600, reference 705071), are used. The microplate cuvettes are washed with 150 mM, pH 7.2 PBS buffer. Next, an aliquot of the solution prepared in Example 3.3.1. is incubated for 24 hours at 4° C. in the cuvettes. After incubation, the cuvettes are washed three times with 150 mM, pH 7.2 PBS buffer, 0.1% Tween-20. The tube is then saturated for two hours at 20° C. with 150 mM, pH 7.2 PBS saturation buffer, 5% BSA. After washing three times with washing buffer, the tubes are dried and stored at 4° C. away from moisture.

For the cuvettes intended for the BlaR-CTD-alkaline phosphatase recognition agent, the washing buffer used is 1 M, pH 9.8 diethanolamine, 0.5 mM $MgCl_2$: for the cuvettes intended for the BlaR-CTD-peroxidase recognition agent, the washing buffer used is 50 mM, pH 5 potassium phosphate.

3.4. Determination of Three Antibiotics in Milk.

1.4 picomol of labelled recognition agent are incubated in the presence of 100 µl of doped milk for 5 minutes at 47° C. The milk is transferred using a pipette into a cuvette which has been pretreated as indicated in Example 2.3. The milk is then incubated for 2 minutes at 47° C. After removing the milk, followed by two washes with washing buffer (cf. Example 2.3.2.), 300 µl of buffer containing the revealing substrate are incubated for 2 minutes in the cuvette (revealing substrate for the BlaR-CTD-peroxidase recognition agent: 50 mM, pH 5 potassium phosphate, 9.1 mM ABTS, 0.002% $H_2O_2$; revealing substrate for the BlaR-CTD-alkaline phosphatase recognition agent: 1 M, pH 9.8 diethanolamine, 0.5 mM $MgCl_2$, 10 mM 4-NPP). The plate is then placed in an automatic spectrophotometer for ELISA plates, the wavelength being set at 405 nm.

This test allows the detection of the three antibiotics penicillin G, cloxacillin and ceftiofur at the control thresholds required by the US authorities (penicillin G at 5 ppb, cloxacillin at 10 ppb and ceftiofur at 50 ppb).

EXAMPLE 4

Determination of the 6 Antibiotics Penicillin G, Ampicillin, Amoxicillin, Cloxacillin, Cephapirin and Ceftiofur in Milk This example illustrates the detection in milk of the 6 antibiotics containing a β-lactam ring which are controlled by the US authorities, down to the standards currently required by these authorities. The test described in this example uses the BlaR-CTD receptor in the form of a fusion protein with alkaline phosphatase or peroxidase, and uses a support in the form of a coated tube.

4.1. BlaR-CTD-Alkaline Phosphatase Fusion Protein
See Example 3.1.

4.2. Solid support: tube coated with a reference antibiotic.
In this example, polystyrene tubes with high protein absorption of the brand name NUNK (Maxisorp type) are used, which are treated with a reference antibiotic solution as indicated in Example 3.3.2.

4.3. Determination of the 6 Antibiotics in Milk.
7 picomol of recognition agent are incubated in the presence of 500 µl of milk for 5 minutes at 47° C. in an Eppendorf tube. The milk is then transferred, using a pipette, into a tube treated as described in Example 3.2. The milk is then incubated for 2 minutes at 47° C. After removing the milk, the tube is washed twice with 1 ml of 1 M, pH 9.8 diethanolamine buffer, 0.5 mM $MgCl_2$. 500 µL of buffer containing the 1 M, pH 9.8 diethanolamine, 0.5 mM $MgCl_2$, 10 mM 4-NPP revealing substrate are then added and the substrate is incubated for 2 minutes at 47° C. The absorbance of the supernatant is then measured using a spectrophotometer whose wavelength is set at 405 nm.

This method allows determination of the 6 antibiotics down to the standards required by the US authorities: penicillin G to less than 5 ppb; ampicillin to less than 10 ppb; amoxicillin to less than 10 ppb; cloxacillin to less than 10 ppb; cephapirin to less than 20 ppb; ceftiofur to less than 50 ppb.

The invention claimed is:

1. A test kit for detecting an antibiotic or antibiotics containing a β-lactam ring in a biological fluid, the test kit comprising:
    at least one recognition agent, which is a receptor which specifically binds to antibiotics containing a β-lactam ring, and is obtained from *Bacillus licheniformis*, and is a BlaR receptor or a BlaR-CTD receptor; and
    at least one reference antibiotic immobilized on a solid support;
    wherein the antibiotic or antibiotics are detected by the test kit in five (5) minutes or less.

2. The test kit according to claim 1, wherein the receptor which specifically binds to antibiotics containing a β-lactam ring is the BlaR-CTD receptor.

3. The test kit according to claim 1, wherein the receptor which specifically binds to antibiotics containing a β-lactam ring is coupled to a labelling agent selected from the group consisting of metallic colloidal particles, colloidal particles of selenium, colloidal particles of carbon, colloidal particles of sulphur, colloidal particles of tellurium, and colloidal particles of colored synthetic latices.

4. The test kit according to claim 1, wherein the receptor which specifically binds to antibiotics containing a β-lactam ring is coupled to a labelling agent which is a fluorescent substance.

5. The test kit according to claim 1, wherein the receptor which specifically binds to antibiotics containing a β-lactam ring is coupled to a labelling agent which is an enzyme.

6. The test kit according to claim 5, wherein the receptor which specifically binds to antibiotics is chemically or genetically coupled to the enzyme.

7. The test kit according to claim 1, wherein the solid support is selected from tubes, plates or rods coated with the reference antibiotic.

8. The test kit according to claim 1, wherein the solid support is a test device comprising:
    a solid support which has a first and second end, to which are attached, successively, starting from the first end,
    a membrane for purifying the biological fluid,
    a membrane on which at least one reference antibiotic is immobilized, and
    an absorbent membrane.

9. The test kit according to claim 1, wherein the solid support consists of a set of magnetic or non-magnetic beads.

10. The test kit according to claim 1, wherein the antibiotic or antibiotics are detected in less than five (5) minutes.

11. The test kit according to claim 1, wherein the antibiotic or antibiotics are detected in three (3) minutes.

12. The test kit according to claim 1, wherein the antibiotic or antibiotics is at least one of penicillin G, ampicillin, amoxycillin or cloxacillin.

13. The test kit according to claim 1, which is capable of detecting penicillin G at a concentration of 3 ppb.

14. The test kit according to claim 1, which is capable of detecting ampicillin at a concentration of 4 ppb.

15. The test kit according to claim 1, which is capable of detecting amoxycillin at a concentration of 4 ppb.

16. The test kit according to claim 1, which is capable of detecting cloxacillin at a concentration of 4 ppb.

17. The test kit according to claim 1, wherein:
    the test kit is capable of detecting penicillin G at a concentration of 3 ppb;
    the test kit is capable of detecting ampicillin at a concentration of 4 ppb;
    the test kit is capable of detecting amoxycillin at a concentration of 4 ppb; and
    the test kit is capable of detecting cloxacillin at a concentration of 4 ppb.

18. The test kit according to claim 2, wherein:
    the test kit is capable of detecting penicillin G at a concentration of 3 ppb;
    the test kit is capable of detecting ampicillin at a concentration of 4 ppb;
    the test kit is capable of detecting amoxycillin at a concentration of 4 ppb; and
    the test kit is capable of detecting cloxacillin at a concentration of 4 ppb.

19. The test kit according to claim 2, wherein the receptor which specifically binds to antibiotics containing a β-lactam ring is coupled to a labeling agent selected from the group consisting of metallic colloidal particles, colloidal particles of selenium, colloidal particles of carbon, colloidal particles of sulphur, colloidal particles of tellurium, and colloidal particles of colored synthetic latices.

20. The test kit according to claim 2, wherein the solid support is a test device comprising:
    a solid support which has a first and second end, to which are attached, successively, starting from the first end,
    a membrane for purifying the biological fluid,
    a membrane on which at least one reference antibiotic is immobilized, and
    an absorbent membrane.

* * * * *